(12) United States Patent
Trepagnier et al.

(10) Patent No.: US 8,014,959 B2
(45) Date of Patent: Sep. 6, 2011

(54) POPULATION OF BACKGROUND SUPPRESSION LISTS FROM LIMITED DATA IN AGENT DETECTION SYSTEMS

(75) Inventors: Pierre C. Trepagnier, Medford, MA (US); Philip D. Henshaw, Carlisle, MA (US)

(73) Assignee: Sparta, Inc., Lake Forest, CA (US)

( * ) Notice: Subject to any disclaimer, the term of this patent is extended or adjusted under 35 U.S.C. 154(b) by 791 days.

(21) Appl. No.: 12/116,673

(22) Filed: May 7, 2008

(65) Prior Publication Data
US 2009/0287418 A1    Nov. 19, 2009

Related U.S. Application Data

(60) Provisional application No. 60/916,466, filed on May 7, 2007.

(51) Int. Cl.
*G01N 33/48* (2006.01)
(52) U.S. Cl. .......................................... 702/19
(58) Field of Classification Search ............. 702/19
See application file for complete search history.

(56) References Cited

U.S. PATENT DOCUMENTS

| | | | |
|---|---|---|---|
| 5,418,951 A | 5/1995 | Damashek | |
| 5,752,051 A | 5/1998 | Cohen | |
| 5,760,406 A | 6/1998 | Powers | |
| 5,968,766 A | 10/1999 | Powers | |
| 6,194,731 B1 | 2/2001 | Jeys et al. | |
| 6,750,006 B2 | 6/2004 | Powers et al. | |
| 7,525,102 B1 * | 4/2009 | Henshaw et al. | 250/393 |
| 2004/0175294 A1 | 9/2004 | Ellison et al. | |
| 2008/0112853 A1 | 5/2008 | Hall | |

OTHER PUBLICATIONS

Trepagnier, et al., "Principal Component Analysis Incorporating Excitation, Emission, and Lifetime Data of Fluorescent Bio-Aerosols," PhAST Conference, Long Beach CA, May 22-25, 2006.
Henshaw, et al., "Background Suppression and Agent Detection in Multi-Dimensional Spaces," PhAST Conference, Long Beach CA, May 22-25, 2006.
Trepagnier, et al., "A Fluorescent Bio-Aerosol Point Detector Incorporating Excitation, Emission, and Lifetime Data," *Proc. SPIE* vol. 6377, 637708 (Oct. 2006).
Henshaw, et al, "Real-time Determination and Suppression of Bio-Aerosol Constituents," *Proc SPIE* vol. 6378, 637814 (Oct. 2006).
Henshaw, et al., "False Alarm Reduction Algorithms for Standoff Detection," Williamsburg Standoff Detection Conference, Williamsburg VA, Oct. 23-27, 2006.
D. Manolakis, et al., "Hyperspectral Image Processing for Automatic Target Detection Applications," Lincoln Laboratory Journal 14 (2003) p. 79.
Keshava, et al., "A Survey of Spectral Unmixing Algorithms," Lincoln Laboratory Journal 14 (2003) p. 55.
Primmerman, "Detection of Biological Agents," Lincoln Laboratory Journal 12 (2000) p. 3.

(Continued)

*Primary Examiner* — Drew A Dunn
*Assistant Examiner* — Stephen J Cherry
(74) *Attorney, Agent, or Firm* — Nutter McClennen & Fish LLP; Thomas J. Engellenner; Reza Mollaaghababa

(57) ABSTRACT

Methods and systems are disclosed for detection of agents such as pathogens or toxic substances and, in particular, to methods and systems for determining the most important background constituents to suppress in a sample, e.g., in a bulk aerosol sample, in order to reduce the probability of false alarms and improve the level of detection of potentially harmful airborne agents.

15 Claims, 6 Drawing Sheets

OTHER PUBLICATIONS

Jeys, "Aerosol Triggers," New England Bioterrorism Preparedness Workshop (Apr. 3-4, 2002).

Lakowicz, Principles of Fluorescence Spectroscopy (Kluwer, New York) 1999.

Sharaf, et al., *Chemometrics* (Wiley & Sons, New York) 1986.

*Applied Optics*, "Laser-Induced Breakdown Spectroscopy," (feature issue) Oct. 20, 2003.

*Existing and Potential Standoff Explosives Detection Techniques*, National Research Council (The National Academies Press, Washington DC) 2004.

Chang, "Orthogonal Subspace Projection (OSP) Revisited: a Comprehensive Study and Analysis," IEEE Trans. Geoscience Remote Sensing 43 (Mar. 2005) pp. 502-518.

Harsanyi, et al., "Hyperspectral Image Classification and Dimensionality Reduction: An Orthogonal Subspace Projection Approach," IEEE Trans. Geoscience Remote Sensing 32 (Jul. 1994) pp. 779-785.

Kwan, et al., "A Novel Approach for Spectral Unmixing, Classification, and Concentration Estimation of Chemical and Biological Agents," IEEE Trans. Geoscience Remote Sensing 44 (Feb. 2006) pp. 409-419.

McCreery, "Spectral Sensing of Bio-Aerosols (SSBA)," available at http://www.darpa.mil/spo/programs/briefing/_SSBA.pdf , as accessed on Mar. 27, 2007.

Keselj, et al., "N-Gram-Based Author Profiles for Authorship Attribution," 2003 Pacific Association for Computational Linguistics.

Grieve, "Quantitative Authorship Attribution: An Evaluation of Techniques," *Literaty and Linguistic Computing*, v. 22, pp. 251-270 (Sep. 2007).

Damashek, "Gauging Similarity with n-Grams: Language-Independent Categorization of Text," *Science* v. 267 pp. 843-848 (Feb. 10, 1995).

Frantzeskou, et al., "Identifying Authorship by Byte-Level N-Grams: the Source Code Author Profile (SCAP) Method," *International Journal of Digital Evidence* v. 6 No. 1 (2007).

* cited by examiner

Fig 5

All Angles Shown in Degrees

| Simulants | S1 | S2 | S3 | S4 |
|---|---|---|---|---|
| S1 | | | | |
| S2 | 72 | | | |
| S3 | 55 | 80 | | |
| S4 | 94 | 38 | 69 | |

| Interferents | S1 | S2 | S3 | S4 |
|---|---|---|---|---|
| I1 | 90 | 112 | 69 | 94 |
| I2 | 73 | 78 | 66 | 80 | 76 |
| I3 | 79 | 71 | 82 | 84 | 86 | 59 |
|  | S1 | S2 | S3 | S4 | I1 | I2 | I3 |

POPULATION OF BACKGROUND SUPPRESSION LISTS FROM LIMITED DATA IN AGENT DETECTION SYSTEMS

RELATED APPLICATIONS

The present application claims priority to U.S. Provisional Patent Application No. 60/916,466 entitled "Population Of Background Suppression Lists From Limited Data In Agent Detection Systems" filed on May 7, 2007, herein incorporated by reference in its entirety.

The present application is also related to a commonly-owned patent application entitled "Selection of Interrogation Wavelengths in Optical Bio-Detection Systems" by Pierre C. Trepagnier, Matthew B. Campbell and Philip D. Henshaw filed concurrently herewith. Both the concurrently filed application and its priority document, U.S. Provisional Patent Application No. 60/916,480, filed May 7, 2007, are incorporated herein by reference in their entirety.

GOVERNMENT RIGHTS

This invention was made with U.S. Government support under contract number HR0011-06-C-0010 awarded by the Department of Defense. The government has certain rights in the invention.

BACKGROUND OF THE INVENTION

The present invention relates generally to methods and systems for detection of agents such as pathogens or toxic substances and, in particular, to methods and systems for determining the most important background constituents to suppress in a bulk aerosol sample in order to reduce the probability of false alarms and improve the level of detection of potentially harmful airborne agents.

The detection of bio-aerosol warfare agents in the presence of either indoor or outdoor backgrounds is a difficult problem. Natural backgrounds are variable and can simultaneously include mixtures of multiple constituents. The variation of each constituent may be larger than the concentration level of an agent whose detection is desired. The detection problems can be further exacerbated by the presence of unpredictable spikes in measurement data of a naturally-occurring background, which may be an order of magnitude larger than the contribution of the normal quiescent background. Such spikes may last for minutes and may exhibit large variations in particle count. The "spike" problem means that temporal filters using recent particle count history to set a detection threshold will not work.

A high false alarm rate creates problems for a bio-aerosol detection system. Repeated false alarms will cause people to panic or begin to ignore warnings. High regret actions, such as building evacuation or administering antibiotics are expensive and create logistics problems if they occur often.

Some bio-aerosol detection systems comprise a trigger plus a confirmation sensor. The trigger is a low-cost, non-specific detection system which runs continuously. The confirmation sensor has high specificity to identify specific bio-agents, and runs only when it is triggered. Typically, confirmation sensors are expensive to operate relative to trigger sensors, and may have logistics requirements for reagents, fluid consumption, etc. A high trigger false alarm rate will drive up the confirmation sensor operating cost. Typically, confirmation sensors will also take longer to provide a result than a trigger sensor. Thus, a trigger sensor with low false alarm rate may be used for low regret actions that need to be taken quickly to be effective such as temporary shut down of a building heat/ventilation/air conditioning system.

One approach to a trigger sensor is to collect a bulk sample, immobilize it, and make high-dimensional measurements of some property of the sample. For example, the high-dimensional space may be the spectrum of reflected or transmitted radiation or the emission spectrum of fluorescence induced by short wavelength illumination. The high-dimensional space may also be the result of concatenated spectra from separate measurements, such as the fluorescence excited by different illumination wavelengths.

Principal component (PC) analysis is a method of reducing the dimensionality of data so that it may be more easily visualized or analyzed. This well-known method uses a data set to determine the direction in the high-dimensional space with the largest variance, the orthogonal direction with the next largest variance, etc., until the remaining dimensions contain only random noise. Each orthogonal direction becomes a component in PC space. Converting additional measurements in the high-dimensional space into PC space is simply a matter of a matrix multiplication once the PC directions are known.

In many cases, there are more than three meaningful principal components. Visualization becomes difficult because at most three principal components can be shown at one time. Viewing multiple graphs provides some indication of the separation of two principal component vectors, but a quantitative measure of the separation is also very useful. One measure, borrowed from hyperspectral imaging, is the spectral angle between two vectors. This angle is defined as the inverse cosine of the normalized dot product of the two vectors. For two vectors $M_i$, $M_j$, the spectral angle between them is given by:

$$SA_{i,j} = \cos^{-1}\left(\frac{M_i \cdot M_j}{|M_i||M_j|}\right).$$

In hyperspectral imaging work, the components of M typically represent raw spectral measurements. Spectral angles can be used to measure separation of two vectors in principal component space. FIG. 5 shows an example of the spectral angles between pairs of interferents and simulants (or agents). This matrix is an example of a Euclidean distance matrix. This matrix can describe distances between vectors which can be plotted on a two-dimensional surface (like the mileage chart on a road map of a small region), or the distances may require a three- or higher-dimensional surface for consistent plotting of the vectors. For example, the mileage chart between cities all over the world would require a spherical surface to place the cities such that all distances were consistent with the mileage chart. The two, three, or higher dimensional space defined by the Euclidean distance matrix of spectral angles is one example of a Simplex, a convex shape defined by corners and edges in a multi-dimensional space.

A linear mixing model provides an appropriate description for the principal components of a typical bio-aerosol, either in-situ or collected and concentrated into a bulk sample. This model also applies to mixtures found on surfaces. The linear mixing model has been used extensively in hyperspectral imaging, where it has been used to describe the measured spectral values directly. The PC values derived from measured spectral values are given by $$M_i = \sum_j a_j E_{ij} + N$$

where
$a_j$ is the abundance coefficient of the $j^{th}$ constituent, and
$E_{ij}$ is the $i^{th}$ principal component of the $j^{th}$ constituent, and
N is a matrix of noise components.

In the model, the values of E for the $j^{th}$ constituent are often referred to as endmembers. These endmembers can be either background constituents, such as pollen, fungal spores, diesel particulates, etc, or they can be chemical or biological agents that we wish to detect. In some cases, simulants can take the place of agents. These simulants are chosen to have signatures which are very similar to the agents that we wish to detect but which are too dangerous to be used in tests. Background constituents which are not agents are often referred to as interferents.

Libraries can be created for agents, simulants, and interferents. These libraries can be created by making measurements of pure substances or by making measurements of real backgrounds. Measurements of pure substances can be made at high signal to noise, under laboratory conditions, with no other background interferents to corrupt the measurements. Pure agents and simulants may be easy to obtain, but pure samples of background constituents must be collected and isolated. Measurement of real backgrounds will not require collection and isolation of individual background constituents, but the signatures of the individual constituents must be separated after detection. This separation of measured data into signatures for individual constituents is one of the important aspects of our invention.

Rotate and suppress (RAS) is a technique to solve the mixture and spike problems. For further details on RAS techniques, see P. C. Trepagnier and P. D. Henshaw, "Principal Component Analysis Incorporating Excitation, Emission, and Lifetime Data of Fluorescent Bio-Aerosols," PhAST Conference, Long Beach Calif., May 22-25, 2006; P. D. Henshaw and P. C. Trepagnier, "Background Suppression and Agent Detection in Multi-Dimensional Spaces," PhAST Conference, Long Beach Calif., May 22-25, 2006; P. C. Trepagnier, P. D. Henshaw, R. F. Dillon, and D. P. McCampbell, "A Fluorescent Bio-Aerosol Point Detector Incorporating Excitation, Emission, And Lifetime Data," SPIE Photonics East, Boston Mass. Oct. 1-4, 2006; P. D. Henshaw and P. C. Trepagnier, "Real-time Determination and Suppression of Bio-Aerosol Constituents," SPIE Photonics East, Boston Mass. Oct. 1-4, 2006; P. D. Henshaw and P. C. Trepagnier, "False Alarm Reduction Algorithms for Standoff Detection," Williamsburg Standoff Detection Conference, Williamsburg Va., Oct. 23-27, 2006 and U.S. patent application Ser. No. 11/541,935, Filed Oct. 2, 2006, entitled "Agent Detection in the Presence of Background Clutter," by P. D. Henshaw and P. C. Trepagnier, all of which are incorporated herein in heir entirety.

To suppress a single background constituent which may have large, unpredictable variations in particle count, we rotate the PC space so that the background constituent is aligned with one of the PC axes. We then drop that axis, eliminating the effect of large particle counts and variations of particle count of that background constituent. If we have multiple background constituents that we wish to eliminate, this process can be repeated. The result is that we trade one PC dimension for each background constituent that we wish to suppress. Because the number of PCs is limited, this means we must choose a subset of the possible interferents to suppress because we cannot suppress an unlimited number of them. The suppression list contains the list of constituents to suppress using RAS. The suppression list can be derived from recent measurements, selected from a library, or a combination of the two. A key aspect of our invention is the strategy of selecting members of the suppression list. In the remainder of our teaching, we will often refer informally to the members of the suppression list as {X} and the maximum length of the suppression list as X.

The "mixture problem" refers to the fact that a spectral measurement M resulting from a mixture of constituents will not be in any of the libraries, and thus will not be directly identifiable as either an agent, a simulant, or an interferent.

An agent detection system must deal with the background environment under different conditions. The system must work very quickly after setup in uncharacterized locations and seasons, for example in battlefield conditions. Performance should be acceptable even without a priori knowledge of the background. Because false alarm rate is a very important parameter for an agent detection system, the system must be able to incorporate limited a priori knowledge of background to improve false alarm performance. This knowledge might include a background library created from measurements in a similar environment, or knowledge that one important background constituent is always present. The system should be able to select constituents to suppress from the background library based on a small number of background measurements. Finally, the agent detection system should be able to improve its false alarm rate over time by learning the background.

Substances known to be present in the background in certain regions of the country are available in pure form from chemical suppliers. These substance include "Arizona road dust," from Powder Technology, Inc., fungal spores ("*Alternaria alternata*"), tree pollen ("Sycamore Eastern Defatted"), grass pollen ("Kentucky Blue Defatted"), "House Dust," and "Upholstery Dust," for example, all available from Greer Source Materials, Lenoir, N.C.

A Government-funded program known as "Bug Trap" collects individual particles, determines which fluoresce, and identifies these as potential background interferents. (Further details can be found on the DARPA website.) The program does not determine the principal components of the fluorescence, but does determine the type of particle if possible. Once the particle type is identified, measurements of pure substances obtained from chemical suppliers could be measured to determine their spectra and resulting principal components.

Hyperspectral imaging (HSI) of the earth's surface has many similarities to agent detection systems. These similarities include the form of the raw data (spectra), background interferents, and the mixture problem. There are important differences between HSI and agent detection, however. First, the images obtained using HSI systems typically have a very large number of pixels (measurements). Our method must work with a smaller number of measurements (tens to hundreds rather than 10,000+). Also HSI must deal with shade problems and atmospheric transmission problems which are not issues for bio-aerosols. Finally, HSI analysis typically includes the time to do field work to identify and measure pure substances (ground truth). (For further details, see N. Keshava, "A Survey of Spectral Unmixing Algorithms," *Lincoln Laboratory Journal* 14 (2003) p. 55.)

Mathematical approaches to determining endmembers developed for HSI include a shrink wrap approach and a simplex approach. In general, these methods tend to underestimate the extent of the distribution, resulting in endmembers which are still mixtures.

Accordingly, there is a need for determination of the members of a suppression list to be used with the RAS background suppression method from a limited number of measured values, with or without a priori information, where the suppression list members will be the most important endmembers of the local, current background mixture.

SUMMARY OF THE INVENTION

In our invention, we populate the suppression list in four different ways, depending on our knowledge of the current background, similar backgrounds, and our background library.

At the start of operations where no a priori knowledge of the ambient background exists, we look at the "X-Most-Recent" independent background constituents, where X is the maximum length of the list of constituents to be suppressed. E.g., if the suppression list is 4 elements long, we will populate it with the 4 most recent background constituents.

An "X-Most-Recent-Plus-Permanent-Members" approach is useful to incorporate some a priori knowledge upon startup, while leaving room on the suppression list for time-varying background constituents. For example, in a post office, paper dust would be ubiquitous, but diesel would appear when doors were opened to load trucks with mail. Fungal spores and pollen could also appear on a seasonal basis when doors to the outside were opened. Thus, paper dust would be an appropriate permanent member in this environment.

An "X-Most-Significant" algorithm becomes appropriate once a collection of background data of reasonable size is available. Because spikes of various background constituents appear at irregular intervals, the "X-most-recent" suppression list may contain recent unimportant constituents which knock the more important constituents off the list. "X-Most-Significant" solves this problem by determining the most likely constituents over a period of time. These most likely constituents are endmembers of the data set. A priori knowledge can be incorporated by using an augmented data set which includes the library of known background constituents. By using this algorithm in combination with a confirmation sensor, never before seen endmembers can be identified as either agents or background constituents and added to the appropriate library.

An "X-Most-Consistent" algorithm requires an extensive background constituent library. This algorithm makes use of a priori knowledge by determining which endmembers from the library are consistent with a small number of samples of background. This algorithm is an option for replacing "X-Most-Recent" more quickly after start-up than the "X-Most-Significant" algorithm.

These algorithms for choosing members of a suppression list, their background library requirements, and their applications are summarized in Table 1.

TABLE 1

| Suppression List Selection Requirements and Applications | | |
|---|---|---|
| Suppression List | Background Library | Application |
| X-Most-Recent | None | Start up - new environment |
| X-Most-Recent-Plus-Permanent-Members | Assumed likely constituents | Start up - environment similar to previously characterized environment |
| X-Most-Significant | Useful in combination with a confirmation sensor to add new members to the library | New environment after data base has been collected |
| X-Most-Consistent | Extensive | Start up after a small amount of data has been collected |

The background library reflects our knowledge of the background. As this knowledge increases, we use it to make better and better choices for the suppression list. This approach will allow a bio-aerosol detection system to be effective immediately upon deployment, and to become more effective with time, learning and adapting to new background interferents and learning to detect new agents. The knowledge of the background can be phased in, with data collection to build the library occurring while the "X-Most-Recent" approach to the suppression list is being used. Note that the "X-Most-Recent" background measurements might be mixtures of background constituents (endmembers). Once sufficient background data has been measured, the "X-Most-Significant" approach to the suppression list provides approximations to actual background constituents (endmembers). These approximations are improved as more data are collected, and can be compared to existing library entries to determine if they should be added to the library. In this way, an extensive library of endmembers is achieved. This extensive library can continue to be used with the "X-Most-Significant" approach to the suppression list for slowly changing environments, or the "X-Most-Consistent" approach to selecting the suppression list can be used for new environments after a small amount of background data has been collected.

Further understanding of the invention can be obtained by reference to the following detailed description, in conjunction with the associated figures, described briefly below.

BRIEF DESCRIPTION OF THE DRAWINGS

FIG. 1 shows a top level view of the background suppression algorithm which incorporates a "rotate and suppress" (RAS) algorithm to suppress the background and a suppression list to specify which background constituents to suppress and which is updated using recent background measurements.

FIG. 2 shows the "X-Most-Recent" method for updating the suppression list, which does not require an interferent library, and which is most useful in a start-up environment. FIG. 2 includes the "X-Most-Recent-Plus-Permanent-Members" method for updating the suppression list, which requires a priori knowledge of one or a few likely background constituents.

FIG. 3 shows the "X-Most-Significant" method for determining the suppression list, which determines suppression list members from the endmembers of a substantial data history.

FIG. 4 shows the "X-Most-Consistent" method for determining the suppression list, which requires an extensive library suitable for a given location, season, and time of day, and which requires a short data history to determine which library members are consistent with recent measurements.

FIG. 5 shows an example of spectral angles calculated for each pair of a seven-member data set.

DETAILED DESCRIPTION

The present invention provides methods and systems for determining the {X} members of a suppression list to be used with a "rotate and suppress" algorithm for background suppression and agent detection. (We refer to this determination as "populating the suppression list.")

Figure 1:
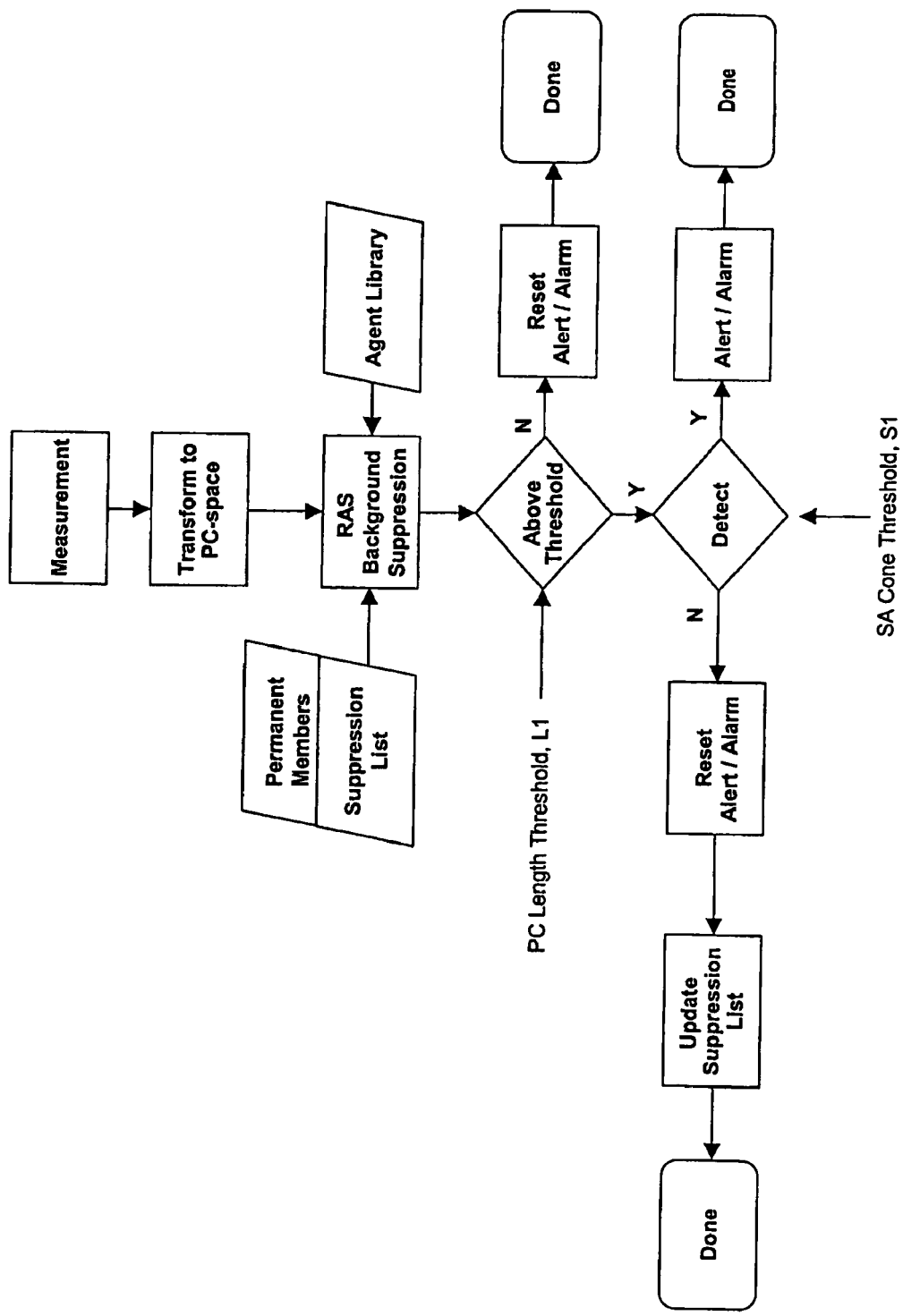

A top level view of the method is shown in FIG. 1. Measurements in raw spectral space undergo a Transform into PC-space using a principal component transformation determined ahead of time using the well-known methods of principal component analysis. Rotate and Suppress (RAS) Background Suppression is performed on both the principal components of the most recent data and the principal components of the Agent Library. Rotate and suppress requires a short Suppression List—typically 3 or 4 constituents long. The suppression list can be populated either from a Background Constituent Library or using the principal components of recent measurements which were not identified as agents. Detection is performed by comparing the rotated and suppressed measurement to the rotated and suppressed agent library using a Spectral Angle Threshold, S1 and a PC Vector Length Threshold, L1.

Each embodiment to be described below makes use of Measurements transformed into Principal Component Vectors and the Spectral Angles between these Principal Component Vectors to determine the elements of the Suppression List.

Figure 2:
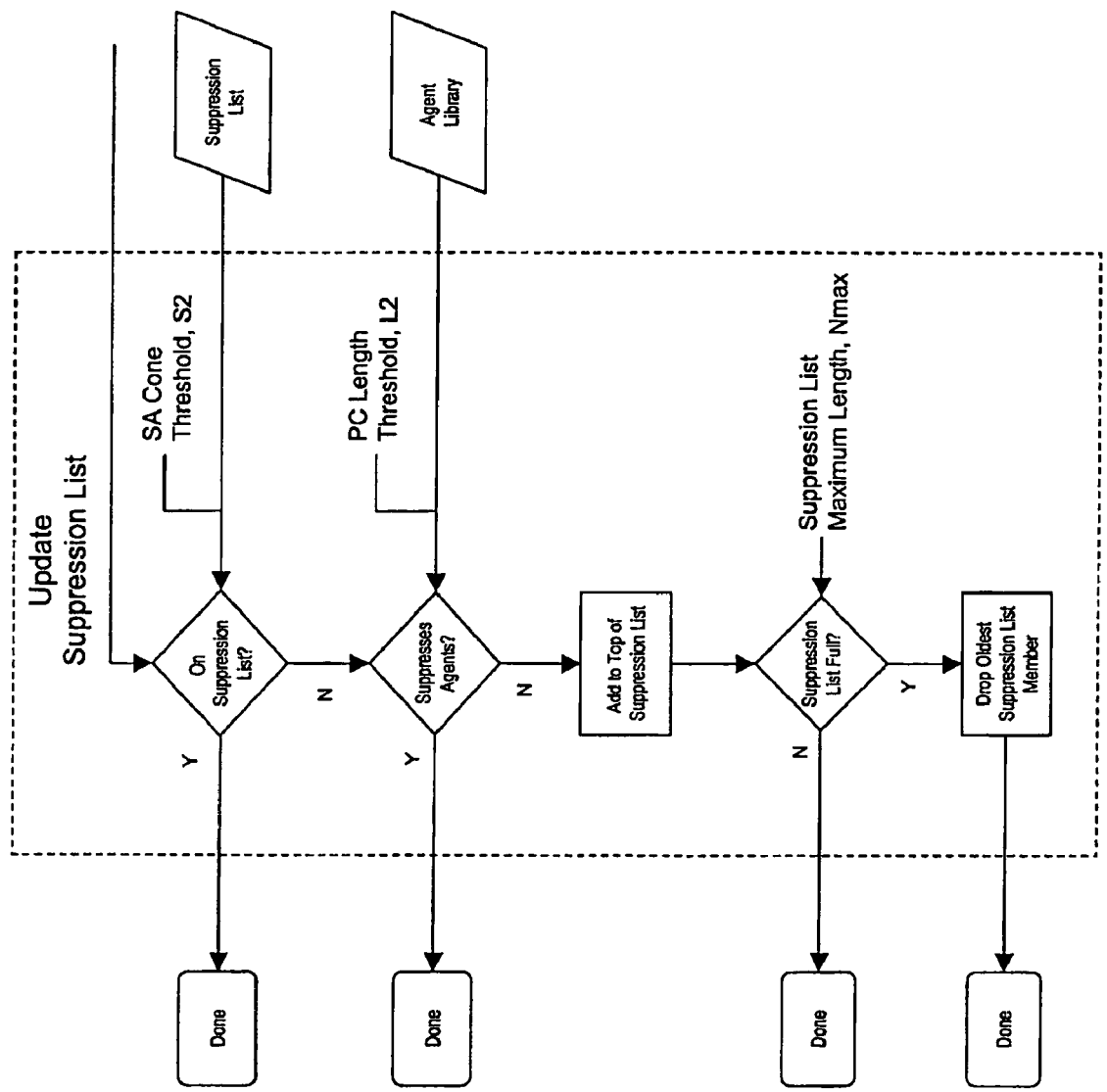

A preferred embodiment for populating the suppression list is "X-Most-Recent-Plus-Permanent-Members" as shown in FIG. 2. This figure shows updating of the Suppression List in the context of a background suppression and agent detection method described in commonly-owned U.S. patent application Ser. No. 11/541,935, Filed Oct. 2, 2006, entitled "Agent Detection in the Presence of Background Clutter." (It should be noted that a more formally correct name might be "(X-P)-Most-Recent-Plus-P-Permanent-Members", since the whole suppression list is X long. In the interest of brevity we have chosen our looser name.) First, we capture a Measurement vector of raw data such as spectral data. Next, these Measurements undergo a Transform to PC-space. The principal components of the Measurements and the Agent Library undergo a RAS (Rotate And Suppress) background suppression using entries in a suppression list, which may include permanent members. The RASed measurements are tested to determine if they are above threshold by comparing to length threshold L1. If not, we reset alert/alarm to the 0 state and the operations on the current measurement are done. The Alert/Alarm state is 0 for no current detection of an agent, advances to 1 for a single detection of an agent from the most recent measurements, and advances to 2 for a second consecutive detection of an agent. This two-state process helps reduce the false alarm rate due to detection noise. If the RASed measurements are above threshold 11, they are passed to a detect step. Typically, detection requires that the RASed principal components of the measurement be within a spectral angle threshold S1, of a RASed agent from the agent library. If the detect conditions are met, the alert/alarm state is incremented by 1 and the operations on the current measurements are done. If the detect conditions are not met, the alert/alarm state is reset to 0, and the principal components of the current measurement are added to the top of the suppression list, just below the permanent members. once the suppression list is updated, operations on the current measurement are done.

It should be immediately apparent that there may be no permanent members on the suppression list. In this case, "X-Most-Recent-Plus-Permanent-Members" is equivalent to "X-Most-Recent."

Figure 3:
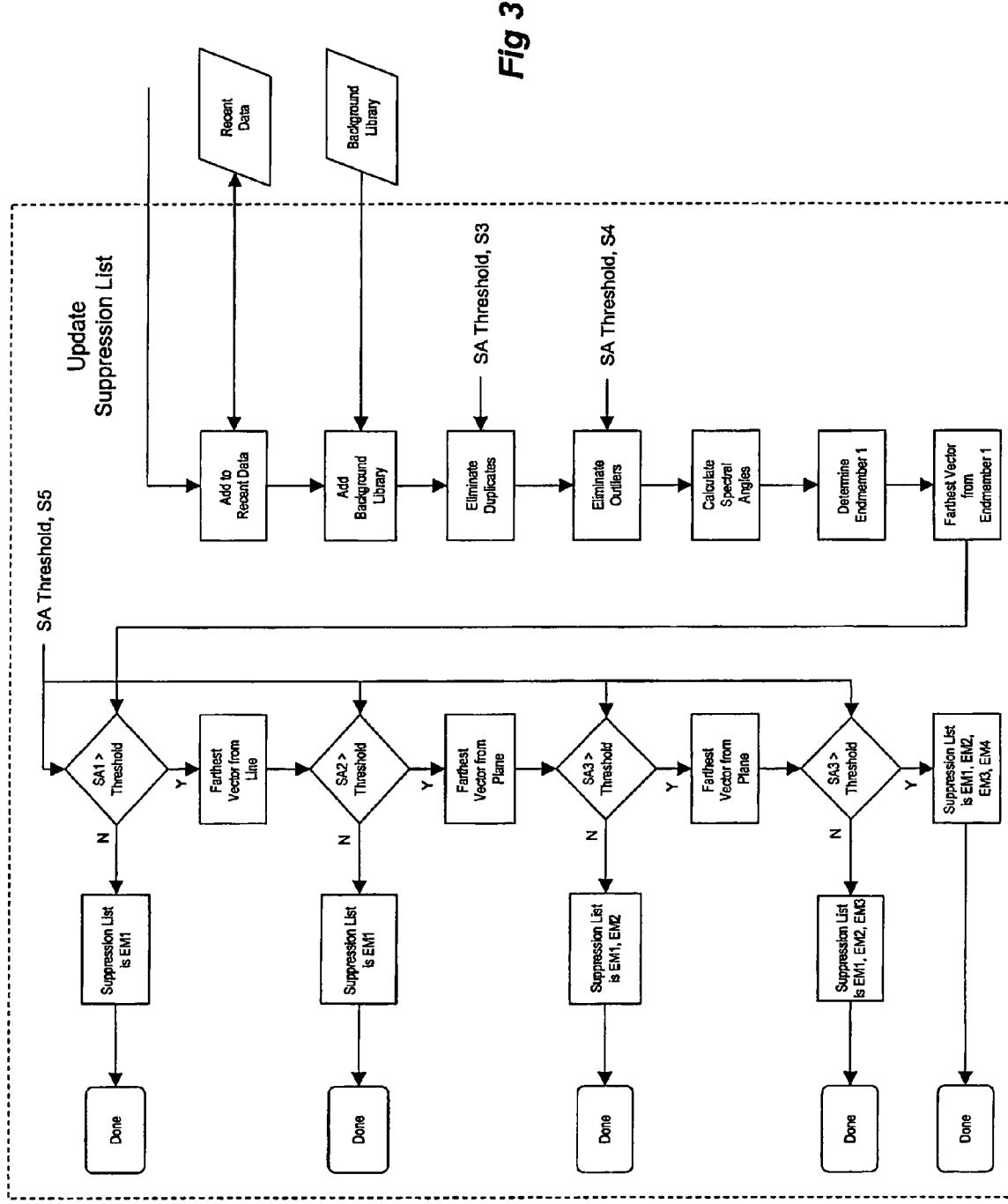

The "X-Most-Significant" method uses a set of principal component vectors to choose the {X} members of the suppression list, as opposed to the "X-Most-Recent-Plus-Permanent-Members" method which uses only one principal component vector at a time. A diagram of this suppression list update method is shown in FIG. 3. The Recent Data set is augmented using the Background Library to add known possible background constituents to the data set. Using the augmented data set, we calculate Spectral Angles between all pairs of vectors in the data set. We Eliminate Duplicates from the data set by eliminating all data set members which are within a very small Spectral Angle Threshold, S3 of another member of the data set. The next step is to Eliminate Outliers by using a Spectral Angle Threshold, S4. Those members of the data set which do not have any neighbors within the Spectral Angle Threshold S4 are eliminated from the data set.

Figure 6:
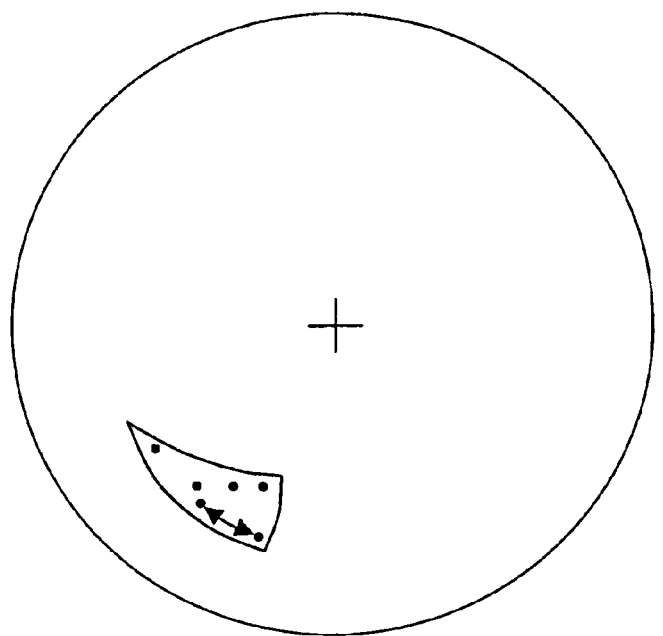
FIG. 6 shows the method for determining endmembers of a substantial data set using only the set of spectral angles between each member of the data set.

The next step is based on the fact that the Spectral Angles between pairs of Principal Component Vectors form a simplex. An example of a simplex in three-dimensional space is shown in FIG. 6. FIG. 6(a) shows a triangular patch on the surface of a unit sphere in three dimensions. For each Principal Component Vector, we calculate a metric mathematically similar in form to a moment of inertia. This calculation is motivated by the observation that Spectral Angle corresponds to distance on the surface of a unit multi-dimensional sphere. For each vector in the data set, the "spectral angle moment of inertia" is given by $$I_j = \sum_{all\ i} (SA_{ij})^2.$$

FIG. 6(b) shows the addition of Background Library Vectors to the data set, indicated by the open circles at the corners of the triangular patch. Using this augmented data set, the spectral angle moment of inertia is used to calculate either a single endmember or the first of several endmembers. If we desire a single endmember, then the vector in the data set with the smallest moment of inertia is a good estimate of that endmember, as shown in FIG. 6(c). Because the moment of inertia calculation is dominated by the largest Spectral Angles with other vectors, the vector with minimum moment of inertia will have small Spectral Angles with most other data vectors and will be near the center of the distribution. If we desire more than one endmember, then the vector with the largest moment of inertia is a good estimate of the first endmember. This vector will have a moment of inertia dominated by several large Spectral Angles and will be at one extreme end of the Principal Component Vector distribution, as shown in FIG. 6(d).

Successive end members can be found by looking for the vectors with the largest spectral angles to the manifold of previously-identified endmembers. For example, a good estimate of the second endmember is the Principal Component Vector farthest in Spectral Angle from the first estimated endmember, as shown in FIG. 6(e). A good estimate of a third endmember is the Principal Component Vector farthest from the line defined by the first two estimated endmembers, as shown in FIG. 6(f). The simplex defined by the Spectral Angles could fill an even higher dimensional space, for example a three-dimensional patch on the surface of a four-dimensional hypersphere. This case cannot be shown as a geometrical drawing, however, a good estimate of a fourth endmember is the Principal Component Vector farthest from the plane defined by the first three estimated endmembers.

Identification of the number of endmembers can be done by calculating four endmembers as described above and graphing the resulting distances of each endmember from the simplex defined by the previously identified endmembers. A Spectral Angle Threshold, S5 is then used to determine the number of endmembers over the range of one to four endmembers as shown in FIG. 3.

Figure 4:
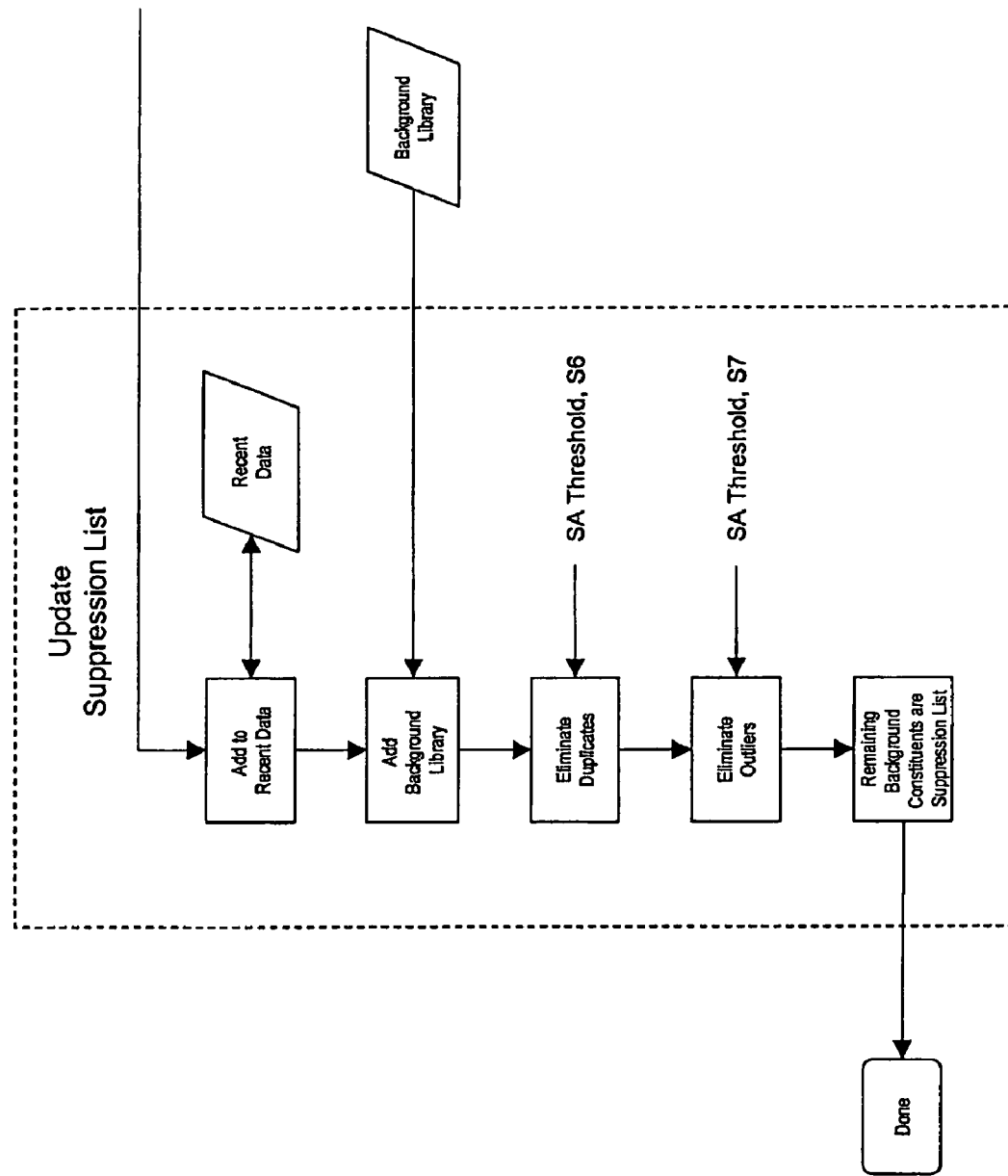

The "X-Most-Consistent" method is shown in FIG. 4. This method makes use of an extensive background library compiled during measurements of the background which could be made at the current location of the bio-aerosol detector or at other locations, seasons, or times of day. This method provides a way to make use of this prior information with a limited amount of background data from the current location. The first step is to collect a small number of measurements from the current location. This Recent Data is transformed to PC-space and processed using RAS to check for an Alert/Alarm using PC Vector Length Threshold L1 and SA Cone Threshold SA1. If no Alert/Alarm occurs, this Recent Data is combined with the Background Library to form a single data base. The complete data base is processed by comparing the spectral angles between data points to a minimum SA Threshold, S6, to Eliminate Duplicates. Once any duplicate points have been eliminated, the spectral angles between the remaining points are compared to an SA Threshold, S7, to Eliminate Outliers which are more than S7 from any other Recent Data or Background Library point. Once this step is complete, any remaining points from the Background Library, but not the Recent Data, become the {X} members of the Suppression List. Any Permanent Members are also kept on the Suppression List.

The teachings of the following publications are herein incorporated by reference: D. Manolakis, D. Marden, and G. A. Shaw, "Hyperspectral Image Processing for Automatic Target Detection Applications," Lincoln Laboratory Journal 14 (2003) p. 79; N. Keshava, "A Survey of Spectral Unmixing Algorithms," Lincoln Laboratory Journal 14 (2003) p. 55; C. A. Primmerman, "Detection of Biological Agents," Lincoln Laboratory Journal 12 (2000) p. 3; T. H. Jeys, "Aerosol Triggers," New England Bioterrorism Preparedness Workshop (3-4 Apr. 2002); J. R. Lakowicz, *Principles of Fluorescence Spectroscopy* (Kluwer, New York) 1999; M. A. Sharaf, D. L. Illman, and B. R. Kowalski, *Chemometrics* (Wiley & Sons, New York) 1986; *Applied Optics*, "Laser-Induced Breakdown Spectroscopy," (feature issue) 20 Oct. 2003; *Existing and Potential Standoff Explosives Detection Techniques*, National Research Council (The National Academies Press, Washington D.C.) 2004; L. S. Powers and C. R. Lloyd, "Method and Apparatus for Detecting the Presence of Microbes and Determining their Physiological Status," U.S. Pat. No. 6,750,006, Jun. 15, 2004; L. S. Powers, "Method and apparatus for sensing the presence of microbes," U.S. Pat. No. 5,968,766, Oct. 19, 1999; L. S. Powers, "Method and apparatus for sensing the presence of microbes," U.S. Pat. No. 5,760,406, Jun. 2, 1998; T. H. Jeys and A. Sanchez, "Bio-particle fluorescence detector," U.S. Pat. No. 6,194,731, Feb. 27, 2001; C-I Chang, "Orthogonal Subspace Projection (OSP) Revisited: a Comprehensive Study and Analysis," IEEE Trans. Geoscience Remote Sensing 43 (March 2005) pp. 502-518; J. C. Harsanyi and C-I Chang, "Hyperspectral Image Classification and Dimensionality Reduction: An Orthogonal Subspace Projection Approach," IEEE Trans. Geoscience Remote Sensing 32 (July 1994) pp. 779-785; C. Kwan, B. Ayhan, G. Chen, J. Wang, B. Ji, and C-I Chang, "A Novel Approach for Spectral Unmixing, Classification, and Concentration Estimation of Chemical and Biological Agents," IEEE Trans. Geoscience Remote Sensing 44 (February 2006) pp. 409-419; For "Bug Trap" see T. McCreery, "Spectral Sensing of Bio-Aerosols (SSBA)," available at http://www-.darpa.mil/spo/programs/briefing/SSBA.pdf, as accessed on 27 Mar. 2007; P. C. Trepagnier and P. D. Henshaw, "Principal Component Analysis Incorporating Excitation, Emission, and Lifetime Data of Fluorescent Bio-Aerosols," PhAST Conference, Long Beach Calif., May 22-25, 2006; P. D. Henshaw and P. C. Trepagnier, "Background Suppression and Agent Detection in Multi-Dimensional Spaces," PhAST Conference, Long Beach Calif., May 22-25, 2006; P. C. Trepagnier, P. D. Henshaw, R. F. Dillon, and D. P. McCampbell, "A fluorescent bio-aerosol point detector incorporating excitation, emission, and lifetime data," SPIE Photonics East, Boston Mass. Oct. 1-4, 2006; P. D. Henshaw and P. C. Trepagnier, "Real-time Determination and Suppression of Bio-Aerosol Constituents," SPIE Photonics East, Boston Mass. Oct. 1-4, 2006; P. D. Henshaw and P. C. Trepagnier, "False Alarm Reduction Algorithms for Standoff Detection," Williamsburg Standoff Detection Conference, Williamsburg Va., Oct. 23-27, 2006; P. D. Henshaw and P. C. Trepagnier, "Agent Detection in the Presence of Background Clutter," U.S. patent application Ser. No. 11/541,935, Filed Oct. 2, 2006, entitled "Agent Detection in the Presence of Background Clutter," by P. D. Henshaw and P. C. Trepagnier; and I. T. Jolliffe, *Principal Component Analysis*, (Springer-Verlag, New York) 1986.

Those having ordinary skill in the art will appreciate that various modifications can be made to the above embodiments without departing from the scope of the invention.

The invention claimed is:

1. A method for detecting a target constituent in a mixture of background constituents, comprising
   utilizing a measurement modality to interrogate the mixture with electromagnetic radiation so as to generate sample spectral data corresponding thereto,
   deriving principal components of the sample spectral data,
   applying a rotate-and-suppress (RAS) transformation to said principal components of the sample data to suppress a contribution of at least one background constituent contained in a suppression list of length X, where X is less than the number of independent components used to describe each constituent, and
   comparing said transformed principal components of the sample data with background-suppressed principal components of corresponding spectral data of a target constituent to determine whether said target constituent is present in the mixture.

2. The method of claim 1 in which the components of each of said target and background constituent is determined by principal component analysis.

3. The method of claim 1 in which N constituents are chosen from recent data and M constituents are chosen from a background library.

4. The method of claim 3 in which the background library includes measurements of known substances.

5. The method of claim 3 in which the suppression list includes N endmembers from a set of recent data.

6. The method of claim 3 in which the N constituents chosen from recent data pass a threshold test.

7. The method of claim 3 in which the background library includes measurements of pure substances and endmembers determined by analysis of mixture data collected from regions of interest.

8. The method of claim 3 in which the N constituents chosen from recent data and the M constituents chosen from a background library do not suppress any members of an Agent Library below a predetermined threshold using the rotate-and-suppress method.

9. The method of claim 3 in which the N constituents chosen from recent data are the N most recent measurements which did not trigger an alert or an alarm, and the M constituents chosen from the background library are permanent members of the suppression list.

10. The method of claim 9 in which the number of significant endmembers is determined by the distances of the respective endmembers from the simplex defined by the next smaller set of endmembers.

11. The method of claim 3 in which a single constituent chosen from recent data has the minimum spectral angle moment of inertia of any member of the recent data set.

12. The method of claim 11 in which a first constituent chosen from recent data has the maximum spectral angle moment of inertia of any member of the recent data set.

13. The method of claim 3 in which the suppression list includes N endmembers from a set of recent data augmented by the constituents contained in the background library.

14. The method of claim 3 in which the suppression list is the set of M constituents from the background library within a spectral angle threshold of at least one significant recent measurement contained in a set of recent measurements.

15. The method of claim 1, further comprising utilizing said measurement modality to obtain spectral data corresponding to at least an agent, deriving principal components of the agent spectral data, and applying said rotate-and-suppress transformation to said principal components of the agent data to generate said background-suppressed principal components of the agent data.

* * * * *